(12) United States Patent
Stringham et al.

(10) Patent No.: US 8,739,601 B2
(45) Date of Patent: Jun. 3, 2014

(54) AIR BUBBLE DETECTOR

(75) Inventors: Mark Stringham, Salt Lake City, UT (US); Roger Millis, West Jordan, UT (US); John Foley, Salt Lake City, UT (US); David Blaine, Holladay, UT (US)

(73) Assignee: Zevex, Inc., Salt Lake City, UT (US)

( * ) Notice: Subject to any disclaimer, the term of this patent is extended or adjusted under 35 U.S.C. 154(b) by 0 days.

(21) Appl. No.: 13/594,142

(22) Filed: Aug. 24, 2012

(65) Prior Publication Data

US 2012/0312072 A1 Dec. 13, 2012

Related U.S. Application Data (62) Division of application No. 12/701,506, filed on Feb. 5, 2010.

(60) Provisional application No. 61/150,706, filed on Feb. 6, 2009.

(51) Int. Cl.
*G01N 29/00* (2006.01)

(52) U.S. Cl.
USPC .......................................... 73/19.03

(58) Field of Classification Search
USPC .............................. 73/1.86, 1.82, 1.83, 19.03
See application file for complete search history.

(56) References Cited

U.S. PATENT DOCUMENTS

| | | | |
|---|---|---|---|
| 3,090,222 A | 5/1963 | Akaboshi et al. | |
| 3,450,476 A | 6/1969 | Rando | |
| 3,974,681 A | 8/1976 | Namery | |
| 3,974,683 A * | 8/1976 | Martin | 73/865.5 |
| 3,987,674 A | 10/1976 | Baumoel | |
| 3,994,599 A | 11/1976 | Southwell | |
| 4,054,255 A | 10/1977 | Magenheim | |
| 4,068,521 A | 1/1978 | Cosentino et al. | |
| 4,277,711 A | 7/1981 | Hanafy | |
| 4,312,341 A | 1/1982 | Zissimopoulos et al. | |
| 4,399,362 A | 8/1983 | Cormier et al. | |
| 4,492,463 A | 1/1985 | Marcuse et al. | |
| 4,559,454 A | 12/1985 | Kramer | |
| 4,618,261 A | 10/1986 | Flanders et al. | |
| 4,651,555 A | 3/1987 | Dam | |
| 4,663,965 A | 5/1987 | Metcalf | |
| 4,673,927 A | 6/1987 | Cianciavicchia et al. | |
| 4,689,986 A | 9/1987 | Carson et al. | |
| 4,722,224 A | 2/1988 | Scheller et al. | |
| 4,762,518 A | 8/1988 | Kreinick | |
| 4,821,558 A | 4/1989 | Pastrone et al. | |
| 4,829,448 A | 5/1989 | Balding et al. | |
| 4,884,065 A | 11/1989 | Crouse et al. | |
| 4,908,676 A | 3/1990 | Bedell et al. | |

(Continued)

FOREIGN PATENT DOCUMENTS

| | | |
|---|---|---|
| EP | 0778465 | 6/1997 |
| JP | 2005-337937 | 12/2005 |
| WO | 89/01796 | 3/1989 |
| WO | 98/04301 | 2/1998 |

*Primary Examiner* — Peter Macchiarolo
*Assistant Examiner* — Tamiko Bellamy
(74) *Attorney, Agent, or Firm* — Hodgson Russ LLP (57) ABSTRACT

Air bubbles may be characterized by an air bubble detector by choosing an optimum set of frequencies and then comparing a return signal from a sensor receiving those frequencies against an internal reference. The number of pulses that exceed the internal reference represents a width and may be counted. The width, as counted, may be correlated to bubble characteristics including volume.

8 Claims, 8 Drawing Sheets

(56) References Cited

U.S. PATENT DOCUMENTS

| | | |
|---|---|---|
| 5,025,222 A | 6/1991 | Scott et al. |
| 5,053,747 A | 10/1991 | Slate et al. |
| 5,074,659 A | 12/1991 | Suzuki et al. |
| 5,116,759 A | 5/1992 | Klainer et al. |
| 5,176,631 A | 1/1993 | Koenig |
| 5,191,795 A | 3/1993 | Fellingham et al. |
| 5,205,153 A | 4/1993 | Hlavinka et al. |
| 5,229,726 A | 7/1993 | Kent |
| 5,233,319 A | 8/1993 | Mizan et al. |
| 5,260,665 A | 11/1993 | Goldberg et al. |
| 5,267,221 A | 11/1993 | Miller et al. |
| 5,351,521 A | 10/1994 | Cracknell |
| 5,392,638 A | 2/1995 | Kawahara |
| 5,394,732 A | 3/1995 | Johnson et al. |
| 5,417,672 A | 5/1995 | Nita et al. |
| 5,422,495 A | 6/1995 | Cohn |
| 5,438,868 A | 8/1995 | Holden et al. |
| 5,442,495 A | 8/1995 | Saito et al. |
| 5,455,565 A | 10/1995 | Moeenziai et al. |
| 5,456,887 A | 10/1995 | Calvo |
| 5,460,178 A | 10/1995 | Hudon et al. |
| 5,475,350 A | 12/1995 | Yamada et al. |
| 5,485,743 A | 1/1996 | Taherian et al. |
| 5,514,102 A | 5/1996 | Winterer et al. |
| 5,531,680 A | 7/1996 | Dumas et al. |
| 5,534,708 A | 7/1996 | Ellinger et al. |
| 5,541,468 A | 7/1996 | Frey et al. |
| 5,672,887 A | 9/1997 | Shaw et al. |
| 5,680,111 A | 10/1997 | Danby et al. |
| D389,228 S | 1/1998 | Winterer et al. |
| 5,704,584 A | 1/1998 | Winterer et al. |
| 5,720,721 A | 2/1998 | Dumas et al. |
| 5,723,773 A | 3/1998 | Bryan |
| 5,733,061 A | 3/1998 | Child |
| 5,746,756 A | 5/1998 | Bromfield et al. |
| 5,764,356 A | 6/1998 | Iwase et al. |
| 5,789,675 A | 8/1998 | Blaine et al. |
| 5,798,050 A | 8/1998 | Gaynes et al. |
| 5,810,323 A | 9/1998 | Winterer et al. |
| 5,844,587 A | 12/1998 | Ando |
| 5,920,007 A | 7/1999 | Hirota et al. |
| 6,023,970 A | 2/2000 | Blaine |
| 6,064,577 A | 5/2000 | Moskowitz |
| 6,068,612 A | 5/2000 | Bowman et al. |
| 6,069,433 A | 5/2000 | Lazarus et al. |
| 6,110,153 A | 8/2000 | Davis et al. |
| 6,110,314 A | 8/2000 | Nix et al. |
| 6,142,008 A | 11/2000 | Cole et al. |
| 6,142,979 A | 11/2000 | McNally et al. |
| 6,192,752 B1 | 2/2001 | Blaine |
| 6,238,347 B1 | 5/2001 | Nix et al. |
| 6,324,889 B1 * | 12/2001 | Fluhrer .......................... 73/1.82 |
| 6,328,720 B1 | 12/2001 | McNally et al. |
| D455,489 S | 4/2002 | Beck et al. |
| 6,396,583 B1 | 5/2002 | Clare |
| 6,408,679 B1 | 6/2002 | Kline-Schoder et al. |
| 6,506,035 B1 | 1/2003 | Beck et al. |
| 6,523,414 B1 | 2/2003 | Malmstrom et al. |
| 6,531,708 B1 | 3/2003 | Malmstrom et al. |
| 6,543,885 B2 | 4/2003 | Bahl |
| 6,595,950 B1 | 7/2003 | Miles et al. |
| 6,623,447 B2 | 9/2003 | Miles et al. |
| 6,636,010 B1 | 10/2003 | Malmstrom et al. |
| 6,659,976 B2 | 12/2003 | Beck et al. |
| 6,685,670 B2 | 2/2004 | Miles et al. |
| 6,709,392 B1 | 3/2004 | Salgo et al. |
| 6,749,591 B1 | 6/2004 | McNally et al. |
| 6,750,468 B2 | 6/2004 | Malmstrom et al. |
| 6,776,763 B2 | 8/2004 | Nix et al. |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,932,114 B2 | 8/2005 | Sparks |
| 6,949,376 B2 | 9/2005 | Kluttz |
| 6,979,311 B2 | 12/2005 | Miles et al. |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| 7,152,482 B2 | 12/2006 | Ueno et al. |
| D536,783 S | 2/2007 | Cise et al. |
| 7,201,870 B2 | 4/2007 | Olsen et al. |
| 7,367,963 B2 | 5/2008 | Cise et al. |
| 2002/0169424 A1 | 11/2002 | Miles et al. |
| 2002/0192111 A1 | 12/2002 | Divino et al. |
| 2004/0220542 A1 | 11/2004 | Cise et al. |
| 2005/0004540 A1 | 1/2005 | McNally |
| 2005/0119625 A1 | 6/2005 | Miles et al. |
| 2006/0058740 A1 | 3/2006 | Cise |
| 2007/0118078 A1 | 5/2007 | McNally |
| 2007/0151346 A1 | 7/2007 | Malmstrom et al. |
| 2007/0167752 A1 | 7/2007 | Proulx et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2009/0049919 A1 | 2/2009 | Hills |
| 2009/0149801 A1 | 6/2009 | Crandall |
| 2009/0192367 A1 | 7/2009 | Braig et al. |
| 2009/0254034 A1 | 10/2009 | Beck |
| 2010/0126275 A1 | 5/2010 | Leyh et al. |

* cited by examiner

AIR BUBBLE DETECTOR

PRIORITY

The present application claims the benefit of U.S. Provisional Application Ser. No. 61/150,706, filed Feb. 6, 2009 which is herein incorporated by reference in its entirety.

THE FIELD OF THE INVENTION

The present invention relates to air bubble detectors. More specifically, the present invention relates to an air bubble detector and related control circuitry with improved sensing and reporting of air bubbles.

BACKGROUND

Bubble detectors have become an important safety feature in many applications including industrial and medical applications. For example, in medical applications, if air is introduced into the bloodstream via an infusion tube, an air embolism may occur. The effects of an air embolism may range from little or no effect to death, typically depending on the amount of air which is introduced. Industrially, it is often desirable to detect the presence of air in a fluid stream to more accurately dose the fluid or to avoid introduction of air into a system. Therefore, it is often useful to automatically detect bubbles.

In the medical field, air bubble detection is often important. Typical applications include dialysis, enteral feeding, and intravenous introduction of fluids. In these situations, the greater the volume of air, the greater could be the risk of harm.

Current bubble detectors send ultrasonic signals through a fluid to detectors and measure amplitude changes on the received signal. The optimum ultrasonic frequency for detection is often different for different situations, as the particular detector, tubing, or fluid may affect the transmission of the signals. Thus, some bubble detectors sweep the entire possible spectrum of ultrasonic frequencies on each pass to reduce the risk of failure in bubble detection. Sweeping the entire spectrum typically results in time spent scanning for bubbles using less than optimal frequencies. The optimum frequency for bubble detection may be affected by piezoelectric crystal proportion, composition, construction tolerances and dynamic factors such as temperature, tubing composition, fluid composition, and the coupling between the sensor and the tube.

False alarms have become a problem in bubble detection. These can be caused by microbubbles that stick to a wall, bubbles that oscillate back and forth in front of a sensor, the decoupling of tubing, etc. False alarms may decrease the trust in the system and increase the workload of staff, and may cause problems or delays in dosing of medication or the like.

SUMMARY OF THE INVENTION

It is an object of the present invention to provide an improved air bubble detector.

According to one aspect of the invention, an air bubble detector is provided which sweeps a frequency range and identifies an optimum frequency which is used to obtain a more accurate characterization of bubbles in the fluid or the volume of air which has passed through the detector.

According to another aspect of the invention, an air bubble detector is provided which measures the amount of time a sensor signal is above a threshold, and which uses the threshold measurement to characterize the air bubble which caused the signal response.

According to another aspect of the invention, a series of bubble detectors are provided which may be used in combination to determine direction and speed of bubbles in the fluid.

These and other aspects of the present invention are realized in an air bubble detector as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The embodiments shown accomplish various aspects and objects of the invention. It is appreciated that it is not possible to clearly show each element and aspect of the invention in a single figure, and as such, multiple figures are presented to separately illustrate the various details of the invention in greater clarity. Similarly, not every embodiment need accomplish all advantages of the present invention.

DETAILED DESCRIPTION

The invention and accompanying drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
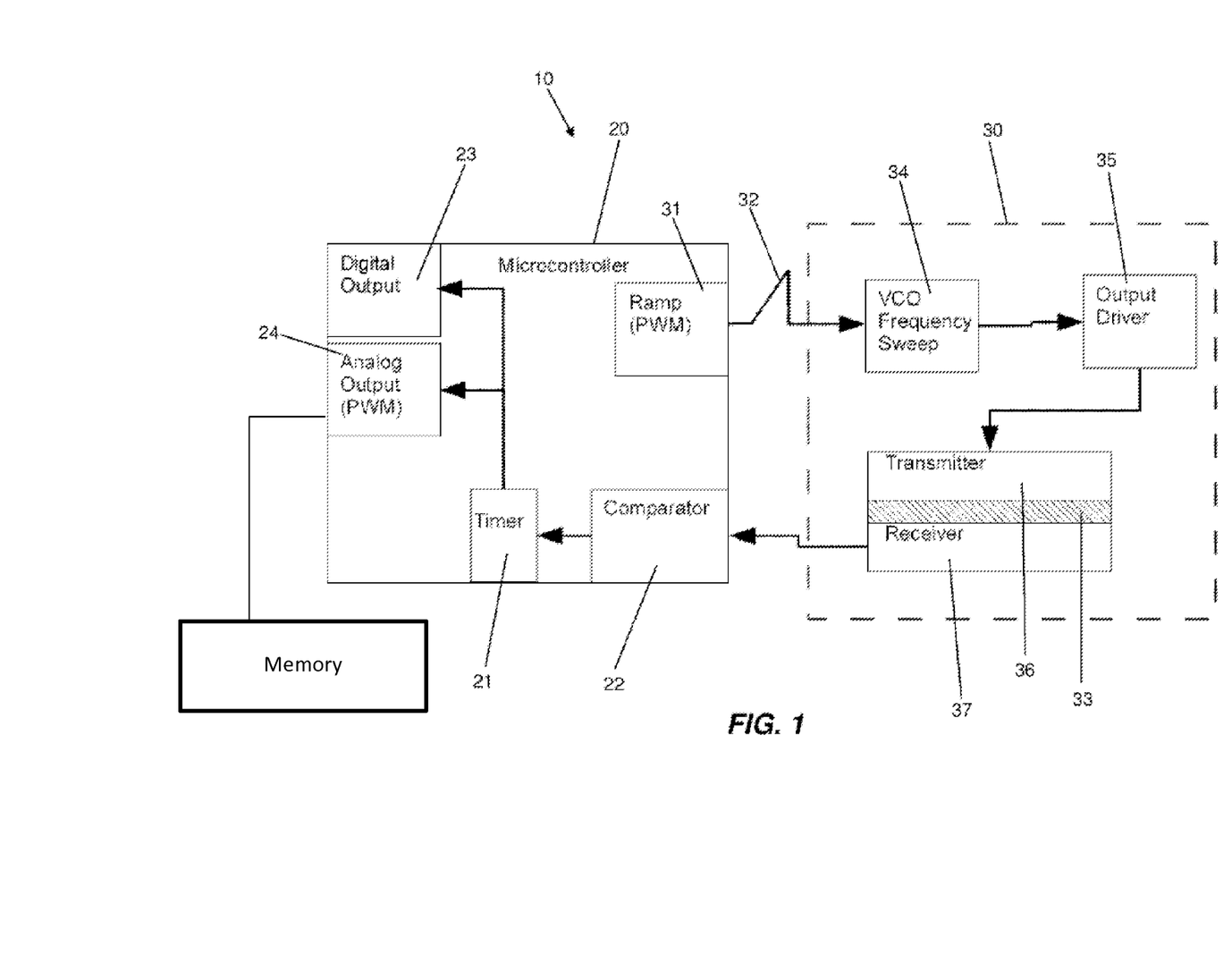
FIG. 1 shows a functional diagram of an air bubble detector.

Turning now to FIG. 1, a functional diagram of an air bubble detector system 10 is shown. The detector 10 includes a microcontroller 20 and a sensor circuit 30. The microcontroller 20 determines the optimum range of scanning frequencies for the detector and operates the detector using this range of frequencies. When operating the detector 10, the controller 20 determines optimal frequencies for scanning and performs scans, recording the duration or width of a signal received which exceeds a predetermined threshold. The controller 20 may periodically scan the entire frequency to update the optimum frequency range used for scanning. The microcontroller 20 sends a signal to the sensor circuit 30 indicating a broad set of test frequencies desired for calibration. The sensor circuit 30 sends back a return signal to the microcontroller based on the transmission of a test frequency range by a sensor through a fluid path 33. An optimum set of operational frequencies is chosen from the test frequencies. Once an optimum range of frequencies is chosen, the microcontroller sends the optimum set of frequencies to the sensor circuit 30 and monitors the return signal from the circuit. For each return signal above an internal threshold value, one is added to a width counter. Based on the width count during the optimum set of frequencies, the microcontroller 20 determines if bubbles are present and characterizes any bubbles in the fluid path 33. Once the optimum set of frequencies have been sent, the width counter is reset and the optimum set of frequencies are resent or the calibration repeated.

In one embodiment, the microcontroller 20 controls the frequencies used for scanning by sending a pulse width modulated (PWM) voltage ramp 32 to the sensor circuit 30. The PWM voltage ramp 32 may direct a voltage controlled oscillator (VCO) 34 to sweep a set spectrum of frequencies. The resulting waveform may be passed through an output driver 35 to isolate the VCO and provide the necessary voltage and current to the transmitter 36, while maintaining waveform fidelity. The transmitter 36, typically a piezoelectric element, receives the electrical waveform signal, and converts it to energy such as ultrasonic waves which are transmissible through the fluid path 33. The receiver 37 detects the transmission of the energy from the transmitter 36 and converts the transmission into a return signal acceptable by the microcontroller 20. According to a preferred embodiment of the invention, the air bubble transmitter 36 and receiver 37 are piezoelectric elements using ultrasonic signals to detect air bubbles.

Inside the microcontroller 20 a comparator 22 receives the signal from the sensor circuit 30 and compares it with an internal reference threshold value. If the signal exceeds the internal reference, one count is added to the width counter. After the sweep of the set optimum spectrum of frequencies, the width counter may be compared to an expected value. This comparison may be correlated with the results of known bubble sizes. The result of the comparison may be output to other devices connected to a digital output 23 or analog output 24. As such, the system 10 can output signal indicative of the size and quantity of the bubble rather than simply outputting receiver pulses.

In one embodiment, the bubble detector is connected with a pump such as an enteral feeding pump. The fluid path 33 consists of a silicone tube with a solution therein. The tube is captured between the transmitter and receiver through friction or a clamping mechanism that fits partially or wholly around the tube without damaging it. The transmitter/receiver pair typically operates on a frequency range from 1.7 MHz to 3 MHz, with a center (optimum) frequency dependent on a specific installation and environment. The frequency range may vary depending on the design of the transducer. For example, many transducers will use the above range, with a resonant frequency of 2 MHz. However, some transducers may have a different resonant frequency such as 3 MHz, such that the sweep range would be shifted up to accommodate the higher resonant frequency. The air bubble detector may be connected to an alarm that may signal a pump, or staff that a bubble has occurred and that action should be taken in response to the bubble. The air bubble detector 10 may also be connected to an information gathering device. In another embodiment, the bubble detector may be connected with an industrial fluid carrying tubing or line and used to monitor bubbles in the fluid as discussed.

Figure 2:
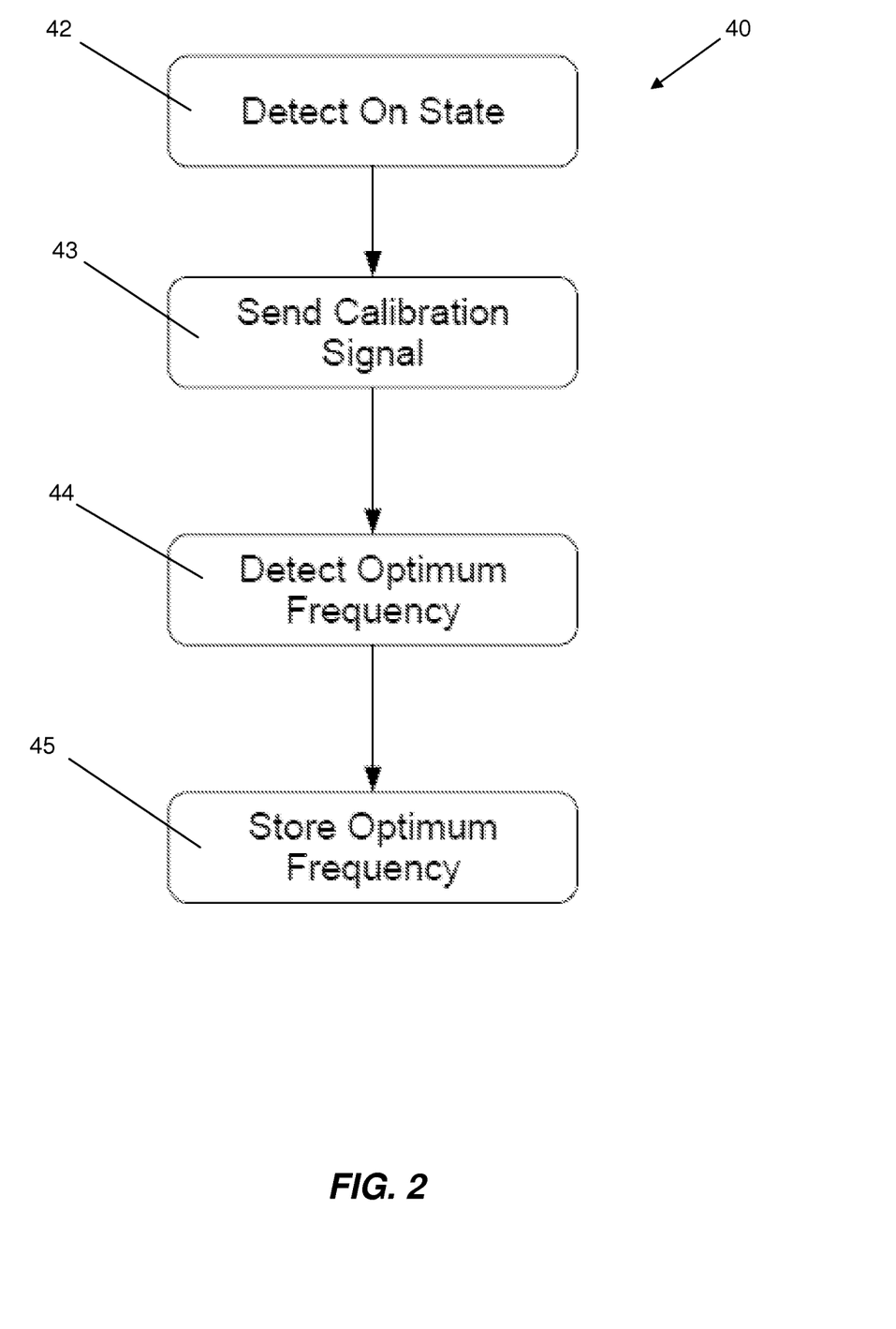
FIG. 2 shows a flow diagram of optimal frequency detection in an air bubble detector.

Turning now to FIG. 2, the process of calibrating an air bubble sensor 40 is shown. Once the air bubble sensor detects an on state 42 or a start signal, a calibration signal 43 is sent to the receiver. The calibration signal 43 includes a sweep of potential ultrasonic frequencies which is used by the sensor 40 to detect air bubbles. The controller circuit 20 creates a ramped signal using a pulse width modulated signal. The ramp signal 32 is sent to a voltage controlled oscillator 34 which converts the voltage ramp into an oscillation signal. The output driver 35 amplifies the signal and transmits the signal to the piezoelectric transmitter 36. Thus, the transmitter 36 transmits a broad range of ultrasonic signals which encompasses the potential operating range for the transmitter 36, receiver 37 and physical system (such as the tube 33 and other physical structures). The optimum frequency is detected 44 by measuring the amplitude of the received signals at the different frequencies and detecting the peak amplitude or amplitudes which correspond to the resonant frequencies for the system. The optimal frequency or frequencies are stored 45 for later use in operating the bubble detector.

The system 10 selects a narrowed range of frequencies for use in scanning for bubbles based on the optimal frequencies. Typically, a predetermined range of frequencies centered around the optimal frequency is used as a set of scanning frequencies. The narrowed range of frequencies is beneficial as it provides increased efficiency and specificity for bubble size, since the scanning is performed using the frequencies which correspond to the resonant frequencies of the system. The use of the narrowed range of frequencies in scanning also increases resolution in the time domain because, for a given sweep rate through the frequency range, the time to scan is less for a narrower range of frequencies. This allows the scan to be repeated quicker, providing a faster scan rate. The measured width of a received signal above a threshold provides information about the bubble size as well as information about the degree of coupling between the tube and the sensor.

The calibration of the sensors during the use of the air bubble sensor may allow for a narrower band of frequencies to be used. The calibration may allow for an optimum frequency to be chosen based on the environmental effects upon the signal transmission. Transmission frequency response may depend on variables that include temperature, transmitter composition and geometry, receiver composition and geometry, fluid path walls, fluid, bubble composition and output strength. Since various conditions such as temperature or fluid composition may change during the use of the device 10, the detector system 10 is often operated by selecting an optimal detection frequency, scanning for a predetermined period of time using the optimum frequency, and then updating the optimal frequency. The optimum frequency is updated by performing a full sweep of the ultrasonic frequency range for the device and selecting new optimal frequencies. The system 10 would not perform this update while a bubble is being detected, as this could interfere with the ability to detect the optimal frequency.

Figure 3:
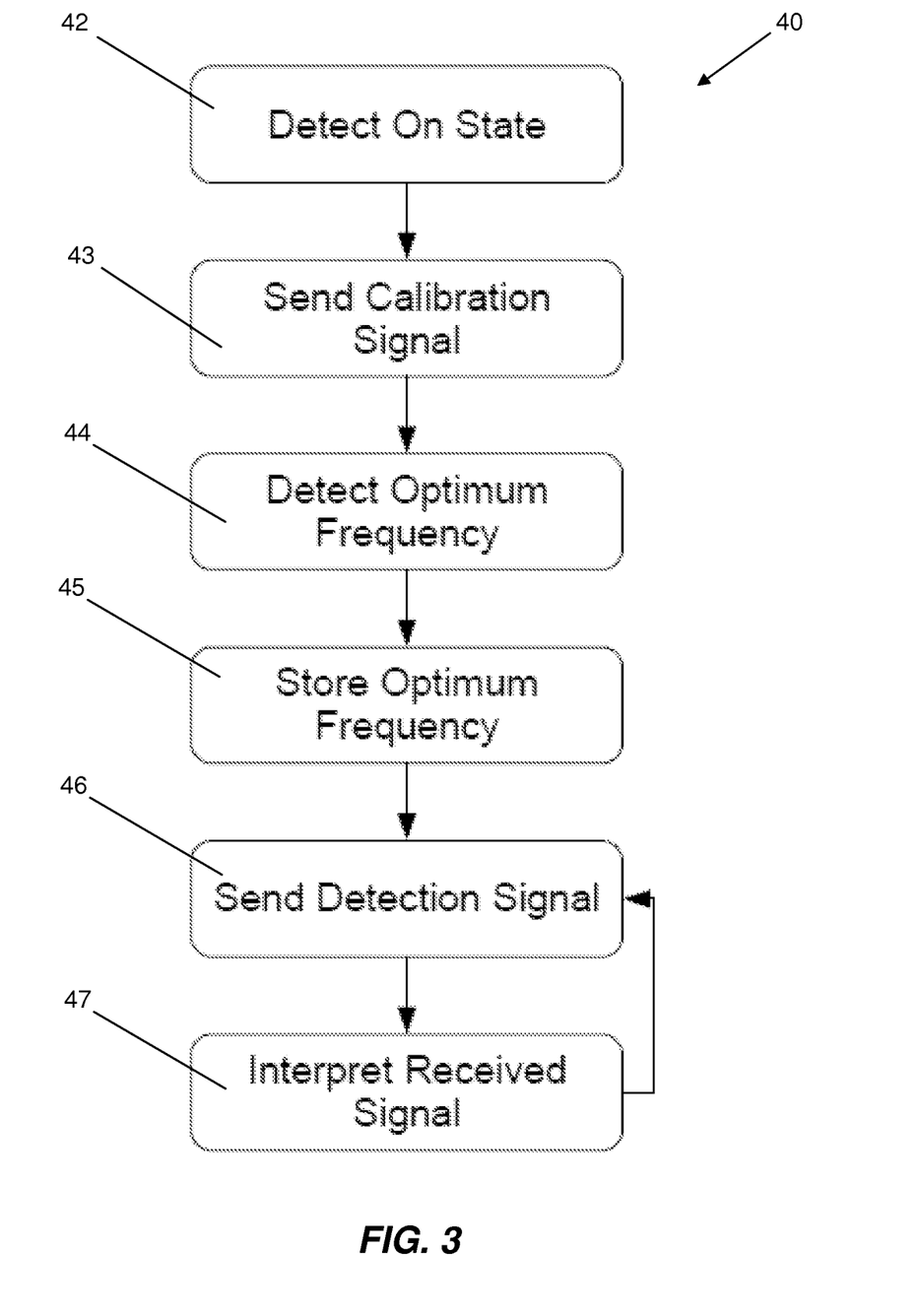
FIG. 3 shows a flow diagram of optimal frequency detection with an increased repetition rate in an air bubble detector.

Turning now to FIG. 3, the calibration and use of the air bubble sensor 10 is shown. The air bubble sensor is calibrated as discussed before by measuring the response to a full frequency signal sweep, and then using the optimum frequencies to narrow the frequency sweep to send a shorter detection signal, as indicated by box 46. The signal is received and interpreted in box 47 faster because the smaller frequency sweep requires less time and allows the data collection and processing to complete faster. Because the frequency sweep is narrowed, the sweep may take less time and the send detection signal step in box 46 and interpret received signal step in box 47 may complete faster. As those steps complete faster, the air bubble detector may detect bubble movement at a higher response rate that allows for accurate readings at higher flow rates within the fluid path than conventional sensors.

The output signal from the receiver 37 is processed by comparison to a threshold value in comparator 22. The threshold value used may be determined during the calibration of the signal frequencies used for scanning. As discussed, a narrowed scanning frequency range is determined by selecting the receiver signal frequencies with the largest values (i.e. the sympathetic or resonant frequencies) and utilizing a predetermined frequency range around these frequencies. When this test is being performed, baseline values for the frequency range may be recorded and used as threshold values. The signals from the receiver 37 are compared to the threshold values to detect a bubble. A bubble has been discussed herein as creating a signal above the threshold value. It will be appreciated that, depending on how the receiver element 37 is referenced and how the signal is transmitted to the comparator 22, a bubble may cause a signal which is either above or below the threshold value. Thus, the term 'above a reference value' is used as a convenient way to refer to signals which deviate from the reference value.

In use, the deviation from the reference signal is monitored and when the deviation exceeds a predetermined value, it is determined that a bubble is present. The comparator determines when a bubble is present by detecting the signals which exceed an allowed deviation from the reference value. The timer 21 shown in FIG. 1 may both control the scanning and operation of the ramp and signal generation circuits as well as the functioning of the comparator. The timer 21 also may perform the function of the counter which counts the time width of the bubble signal. That is to say that, for each time unit where the receiver signal exceeds the reference value and indicates a bubble, the counter adds a count to the count total. The count total indicates the total size of the bubble, and is thus used to characterize the bubble. When the bubble passes and the receiver signal returns to the threshold value, the counter is reset.

Figure 4:
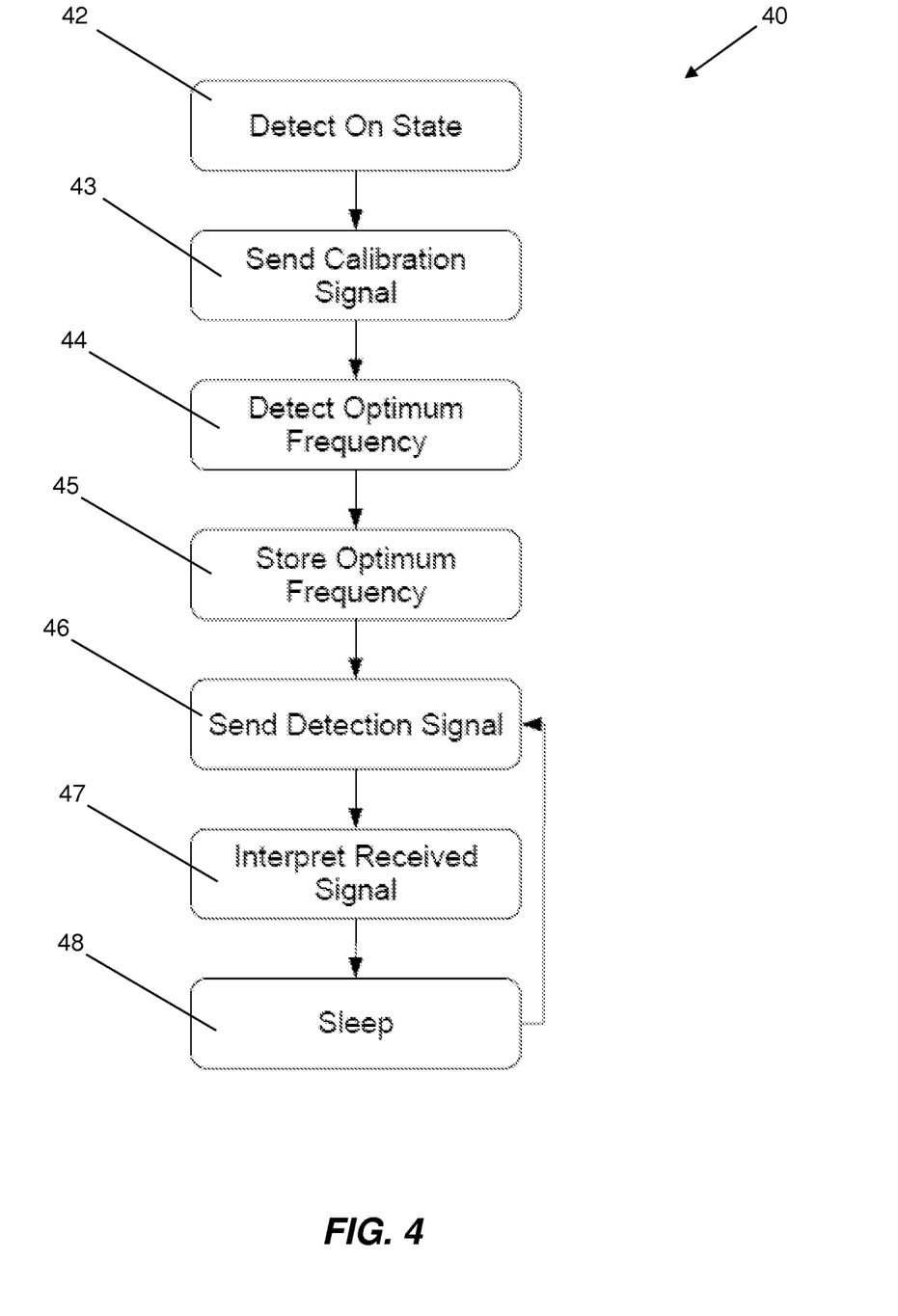
FIG. 4 shows a flow diagram of optimal frequency detection with a battery saving sleep state in an air bubble detector.

Turning now to FIG. 4, a method of using the air bubble detector system 10 is shown that may result in decreased power usage. The air bubble sensor is calibrated as discussed above. The optimum frequencies are used to narrow the frequency sweep used for detection of bubbles, resulting in a detection signal with a shorter time duration as seen in box 46. The signal is received and processed as indicated in box 47. Instead of immediately sending the next detection signal 46, the air bubble detector may enter a powered down state or sleep state as seen in box 48. Because the detector 10 operates using a narrow band of optimum scanning frequencies, the time to complete a single scan may be microseconds. The time duration where a bubble may be between the transmitter 36 and receiver 37, however, may be fractions of a second. Thus, the detector may complete a scanning cycle in a few milliseconds or less, power down for a hundred milliseconds, and then perform the next scan cycle. The powered down state may require less power for the inactive cycle time, resulting in a more efficient use of power and even decreased power requirements.

The decreased power usage is useful in situations that require battery power or sensitivity to the transmitted energy. As the optimum set of frequencies is merely a selection of frequencies of the total possible frequencies, the air bubble detector may only cause periodic transmissions as required by the flow rate within the fluid path. Thus the battery drain is reduced.

Communication may exist between the air bubble detector and a pump which is driving the flow within the fluid path. The repetition rate of the air bubble detector is influenced or controlled by the pump. Thus, the pump may operate the detector system 10 such that, as the flow rate increases, the scan repetition rate may increase as well. As the flow decreases, the air bubble detector may operate at a slower scan repetition rate.

Figure 5:
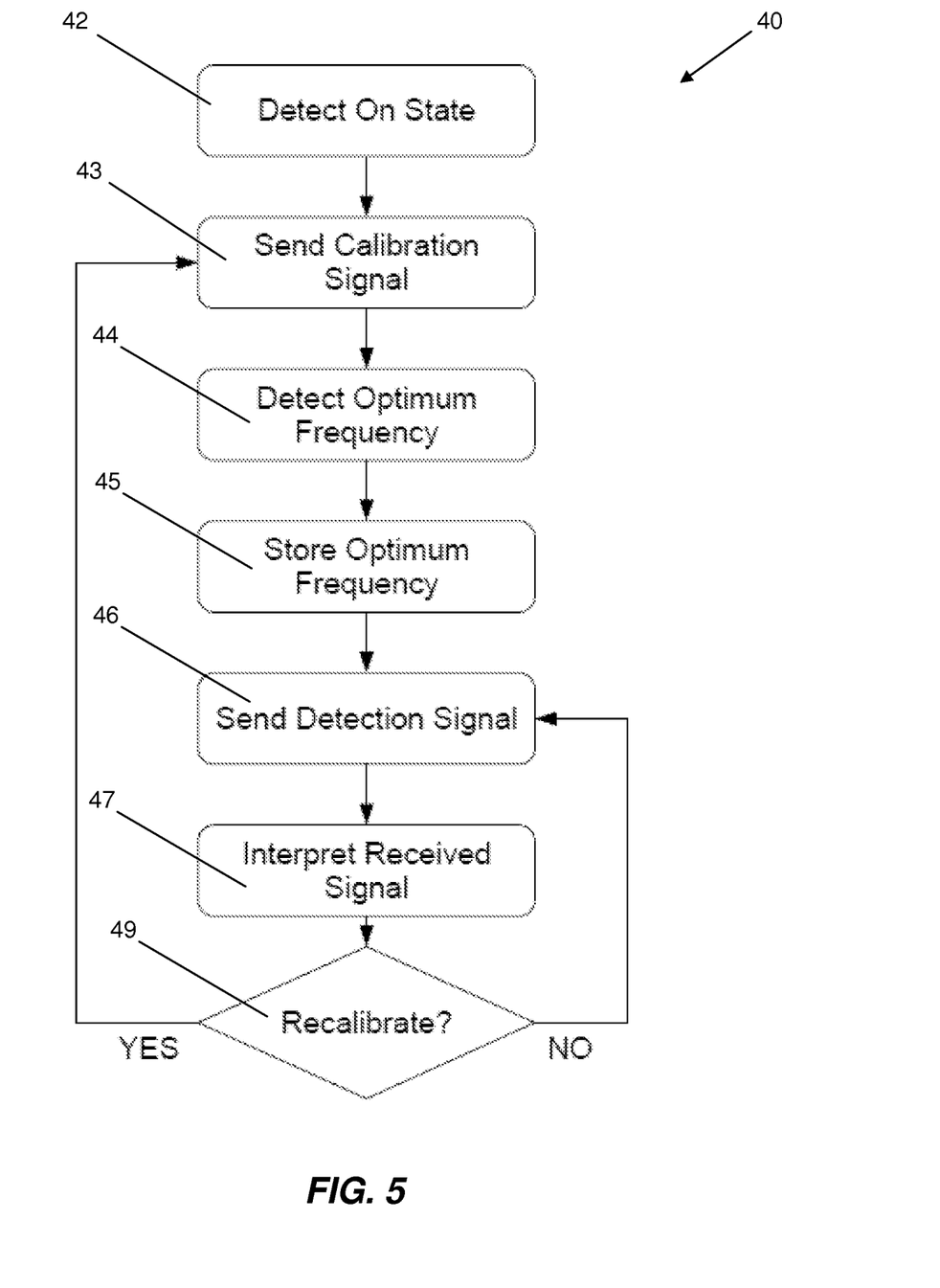
FIG. 5 shows a flow diagram of recalibrating optimal frequency detection in an air bubble detector.

Turning now to FIG. 5, it is shown how the system 10 may operate to periodically calibrate the air bubble sensor. The initial calibration and detection proceed as before. After interpreting the received signal in box 47, the air bubble detector determines if a recalibration is required in box 49. This recalibration is determined by a pre-specified time period, changes noted in the environment, degradation of the received signal or external request from a user. The recalibration may allow the air bubble detector to adapt to changing environmental conditions while maintaining its enhanced performance.

Figure 6:
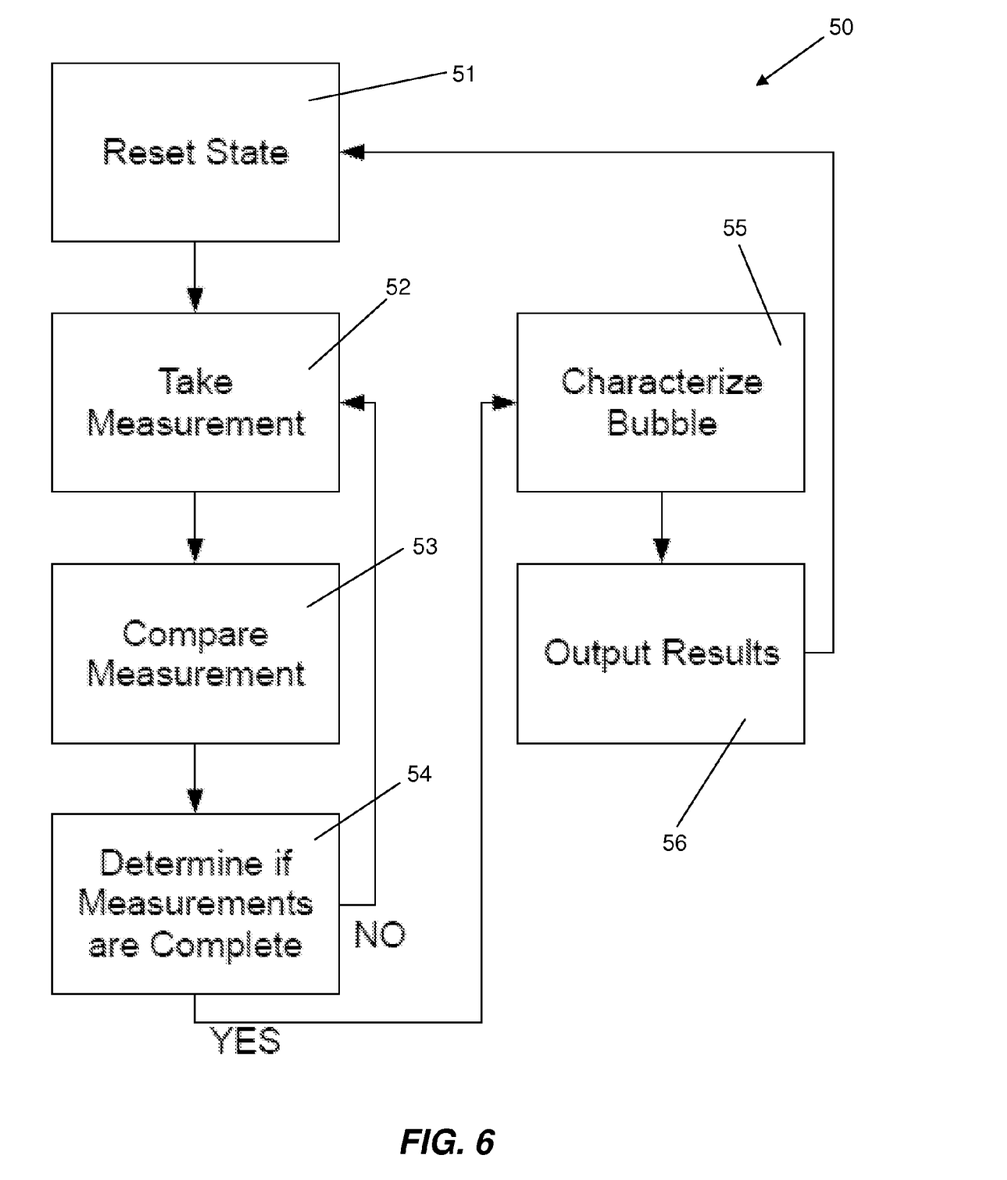
FIG. 6 shows a flow diagram of bubble characterization through measurement of time.

Turning now to FIG. 6, the process of detection of an air bubble 50 by the air bubble detector is shown. The air bubble detector begins by resetting its state in box 51 to prepare for a new set of measurements. As a measurement is taken in box 52, the measurement is compared against an internal reference in box 53. The air bubble detector stores this information about whether each comparison exceeds the internal reference. When enough measurements have been taken, the air bubble detector will use the measurements to characterize any bubble detected in box 55 and output the results in box 56. The system can track long term changes in the received signal and thus adjust for the signal threshold used to detect bubbles or recalibrate the frequency range used to detect bubbles. The short term changes in the received signal are used to detect bubbles.

One advantage of storing information related to whether a set of measurements exceeds an internal reference is a decreased sensitivity to environmental effects causing changes in amplitude. Instead of measuring a potentially noisy signal amplitude, the number of times the signal passes a preset standard is recorded. This duration measurement, or width measurement is correlated to bubble size. Using the volume calculation, the volume of a series of bubbles is added together for a total volume measurement. The microcontroller may then set a limit on bubble size, total air volume, volume within a time period, or a combination depending on the application.

The output of the air bubble detector is digital, analog, data or any combination of these. The microcontroller may use a PWM driver or digital to analog converter to generate an analog voltage or current output signal. The analog output could convey to the host system the various bubble sizes that are detectable by the sensor. The digital output may transmit similar or more complete data to a host system using any number of protocols including SPI, I2C or others.

Figure 7:
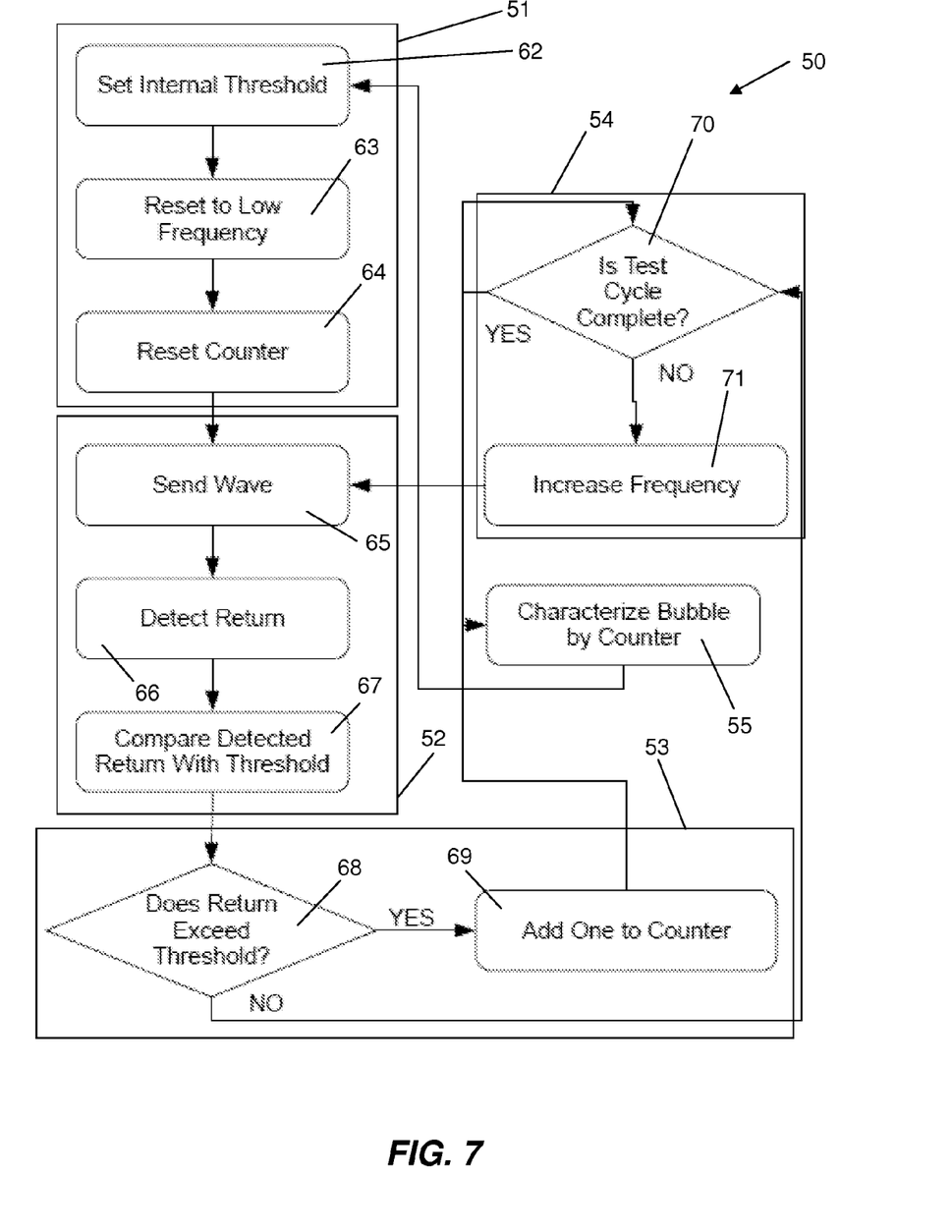
FIG. 7 shows the flow diagram of FIG. 6 broken down into more specific processes.

Turning now to FIG. 7, the process of FIG. 6 as broken down into more specific processes is shown. The same process of resetting state in box 51, taking a measurement in box 52, comparing the measurement in box 53, determining if the measurements are complete in box 54, and characterizing the bubble in box 55 are shown with more incremental steps.

By resetting its state in box 51 the air bubble detector may prepare to take new measurements. In one embodiment, the reset state in box 51 is performed along with determining the internal threshold in box 62 that may result in a return signal being counted as a bubble in the width measurement. The frequencies to be swept setting is reset to start at the low frequency in box 63. The width counter may also be reset in box 64.

Small bubbles are detected based on the width of a received signal at a threshold signal level. Long term changes in the width of the signal at the threshold level is used to adjust the bubble size estimate. To begin accumulating for large bubbles which would result in several received signals with a signal level above the threshold, the initial signal width could serve as a trigger to start accumulating multiple received signals together to determine the size of a large bubble.

The internal threshold may act as a barrier to noise. If the internal threshold is too low, noise may cause a small signal amplitude to be counted as a bubble, producing a false width. Similarly, if the internal threshold is too high, the return signal may not have enough amplitude to exceed the internal threshold and bubbles may not be counted. Therefore an internal threshold is selected above the noise but less than the return signal amplitude to avoid these problems.

After resetting state in box 51, the air bubble detector may take measurements in box 52. In one embodiment, the air bubble detector may transmit a wave through the fluid path in box 65. The wave is detected in box 66 and sent to be compared with an internal threshold in box 67.

The transmitter/receiver pair may differ somewhat depending on the fluid path, and typically is an ultrasonic transmitter and receiver, such as a pair of piezoelectric elements. The specific choice of technology may depend on the ability of the chosen sensor pair to penetrate different parts of the fluid path. Such considerations may include the fluid path walls, the fluid itself and the bubbles within.

After taking measurements as seen in box 52, the air bubble detector may compare the measurements in box 53. In one embodiment, the measurements is compared with an internal threshold in box 67. The air bubble detector may compute whether the return signal exceeds the internal threshold in box 68. If the return signal does exceed the threshold, one is added to the width counter in box 69 and then processing may continue in box 70. If the return signal does not exceed the threshold, processing may move to box 70.

After comparing the measurements in box 53, the air bubble detector may decide whether the measurements are complete in box 54. If, in box 70, it is decided that the measurements are not complete, the air bubble detector may move to the next frequency in box 71 and then return to box 65 to send the next wave. If the test cycle is complete, the air bubble detector will move to box 55 to use the information collected from the measurements.

The decision on whether to complete the test cycle in box 70 may include the end of a frequency sweep, detected failure in the system or enough data to characterize the bubble. In one embodiment, the air bubble detector may repeatedly sweep a frequency spectrum. The test cycle is complete when the frequency spectrum has been swept. In another embodiment, a detected failure in the system may cause the test cycle to complete and then reset. In some systems this wait to reset is required because an output is expected at certain intervals. An immediate reset may not be possible because a watchdog timer may cause an undesirable full system reset due to a missed output timing. In another embodiment, sufficient data may exist to characterize a bubble, such as a total occlusion of the fluid path by the bubble, and a full sweep is not required.

After the decision in box 54 results in the cycle being complete, the air bubble detector may characterize the bubble in box 55. The received signal is proportional to the width counter. Thus, the width measurement may contain information related to signal strength. In one embodiment, the stronger the received signal, the greater the width is. As a bubble moves through the sensor the signal strength may decrease that may also be manifested in the width decreasing. A bubble size is correlated with a width much like an existing sensor correlates amplitude to bubble size.

In one embodiment, the air bubble detector is connected in line with an intravenous infusion line. The tube is captured between the transmitter and receiver through friction or a clamping mechanism that fits partially or wholly around the tube without damaging it. The transmitter/receiver pair may operate on an acoustical frequency from 1.7 MHz to 3 MHz. As a bubble moves through the sensor the signal strength may decrease, which causes the measured width to decrease. Should the measured width decrease enough, an alarm is alerted to the problem.

While the processes described above may appear linear in this description for ease of understanding, the actual steps are performed in parallel. For example, in one embodiment, the characterization of the bubble may work in parallel with the next detection of bubbles as seen in boxes 51-54. This will allow for a further gain in repetition rate. Thus, the tasks described may run in parallel with the tasks described or with other tasks not included in this disclosure.

While the specific embodiments described may use a single sweep of frequencies to determine bubble presence, multiple sweeps of the frequencies are used to characterize a bubble or set of bubbles. The width is stored in multiple counters that are used to perform a final determination of bubble volume. In one embodiment, the width counters are used on a rolling basis to average out the effects of noise.

In another embodiment, multiple sensors are attached to the fluid path allowing the air bubble detector to detect bubble flow direction, speed and flow rate. The different sensors are placed upstream/downstream from each other, and may thus detect the bubble as it flows through the tubing. The information gathered from multiple sensors may also prevent alarms from microbubbles that stick to a wall, sticky bubbles, and bubbles that oscillate back and forth in front of a sensor. Since, in these cases, only one sensor would detect the bubble (at least for a period of time before the bubble eventually moves), the system would identify this as a single bubble and not many different bubbles, preventing false alarms due to an incorrectly high bubble count. The alarm is triggered by a bubble that has been characterized by one sensor and then sensed by another. Often, bubbles or the like which are not moving towards the patient through the tube should not trigger the alarm or stop the fluid flow. In the event that the bubble does begin to move towards the patient, the bubble would be counted.

In another embodiment, the air bubble sensor may communicate with an external device that measures or knows the flow rate of the liquid. The air bubble sensor may adjust its repetition rate in accordance with the information given by the external device. Such external devices may include a pump, flow sensor or manual input. This communication may also prevent alarms from the decoupling of tubing as sensed by the external device.

Figure 8:
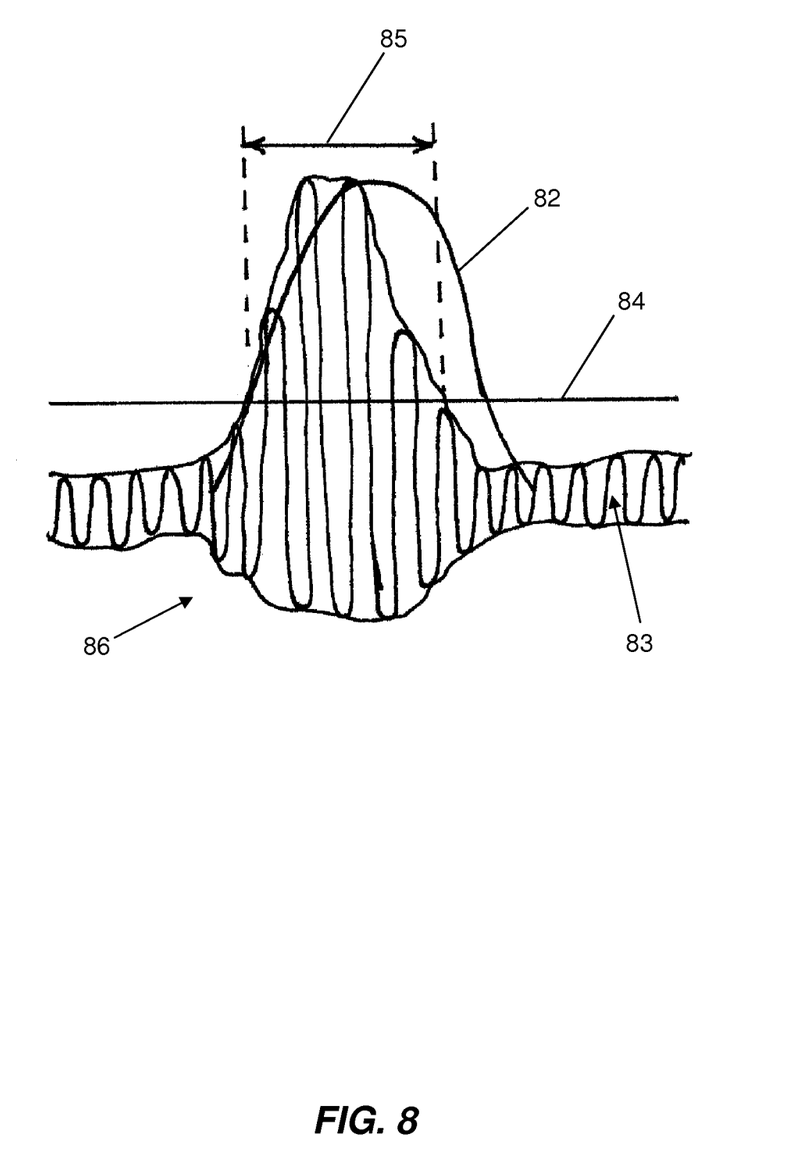
FIG. 8 shows a comparison between an expected signal and a received signal.

Turning now to FIG. 8, a reference signal 82 compared with a received signal 83 is shown. The air bubble detector may measure the received signal by the number of counts crossing the voltage reference threshold 84 which it reads during a frequency sweep. The measurement may result in the width 85 of the received signal with respect to the internal voltage reference setting 84 and reference signal 82 for a known bubble size, tubing set, and loading conditions. The received signal envelope 86 may then be proportional to the reference signal 82. This proportionality may result in the width measurement containing information related to signal strength or bubble size.

It may also be appreciated that the initial selection of optimum frequencies may provide advantages to characterizing the bubble. As a result of the frequency selection and repetition rate, bubbles are more accurately measured by the width counter. In fact, one advantage may include a more granular volume result due to an increased speed of the measurements.

The signal shown and discussed with respect to FIG. 8 can also be used to determine if a tube is properly loaded in the sensor, and thus in the pump or device. The receive signal amplitude is at low level if no tubing is loaded in the sensor, at a high level if fluid-filled tubing is loaded in the sensor, and at an intermediate level (typically close to but distinguishable from the low signal level) for tubing which is loaded in the sensor but which has a bubble present within it.

There is thus disclosed an improved air bubble detector. It will be appreciated that numerous changes is made to the present invention without departing from the scope of the claims.

What is claimed is:

1. A bubble detection system comprising:
   a fluid path;
   a piezoelectric transmitter and a piezoelectric receiver disposed adjacent the fluid path for detecting bubbles therein; and
   control circuitry for operating the transmitter and receiver comprising:
     a circuit for generating a wide range frequency sweep in the transmitter;
     a circuit for analyzing the receiver output and determining a resonant frequency for the piezoelectric transmitter and receiver and fluid path;
   memory for storing the resonant frequency;
     a circuit for operating the transmitter at a reduced frequency range at the resonant frequency in order to thereby detect bubbles in the fluid path:
     a comparator circuit for comparing the receiver signal while detecting bubbles to a signal threshold to determine if bubbles are present;
     wherein the comparator circuit determines the time period for which a signal exceeds the signal threshold and determines bubble size based on the time period.

2. The system of claim 1, wherein the circuit for generating a wide range frequency sweep in the transmitter comprises a voltage ramp generating circuit and a voltage driven frequency generation circuit.

3. The system of claim 1, wherein the fluid path comprises a tube for delivering a liquid.

4. The system of claim 1, wherein the circuit for analyzing the receiver out and determining a resonant frequency for the piezoelectric transmitter and receiver and fluid path comprises a comparator circuit.

5. The system of claim 1, further comprising a medical pump configured to pump fluid through the fluid path.

6. The system of claim 5, wherein the control circuitry is configured to control the transmitter to send the wide range frequency or the reduced frequency range at a time that is based upon a flow rate of the fluid through the fluid path.

7. The system of claim of claim 1, wherein the piezoelectric transmitter and piezoelectric receiver includes a plurality of piezoelectric transmitters and a plurality of piezoelectric receivers spaced along the fluid path.

8. The system of claim 7, wherein the plurality of piezoelectric transmitters and the plurality of piezoelectric receivers are spaced at regular intervals along the fluid path.

* * * * *